United States Patent [19]

Daneshvar

[11] Patent Number: 5,603,700
[45] Date of Patent: Feb. 18, 1997

[54] SUCTION AND INJECTION SYSTEM

[76] Inventor: Yousef Daneshvar, 21459 Woodfarm, Northville, Mich. 48167

[21] Appl. No.: 172,754

[22] Filed: Dec. 27, 1993

[51] Int. Cl.⁶ .............................. A61M 1/00; A61M 5/00
[52] U.S. Cl. ........................ 604/122; 604/33; 604/249
[58] Field of Search .......................... 604/122, 207, 604/227, 246–249, 256, 33, 38

[56] References Cited

U.S. PATENT DOCUMENTS

| | | | |
|---|---|---|---|
| 458,774 | 9/1891 | Lottridge | 604/38 |
| 931,113 | 8/1909 | Bean | 604/38 |
| 1,314,855 | 9/1919 | Carpenter | 604/33 |
| 1,831,668 | 11/1931 | Juhl | 604/248 |
| 2,032,723 | 3/1936 | Schweser | 604/248 |
| 2,485,842 | 10/1949 | Pennington | 604/248 |
| 4,047,527 | 9/1977 | Kelsen | 604/249 |
| 4,193,406 | 3/1980 | Jinotti | 604/33 |
| 4,414,999 | 11/1983 | Basta | 604/249 |
| 4,497,468 | 2/1985 | Hubbard et al. | 604/249 |
| 4,662,868 | 5/1987 | Cambio, Jr. | 604/38 |
| 4,668,215 | 5/1987 | Allgood | 604/33 |
| 5,034,000 | 7/1991 | Freitas et al. | 604/249 |

FOREIGN PATENT DOCUMENTS

0414825  8/1934  United Kingdom ................ 604/248

*Primary Examiner*—C. Fred Rosenbaum
*Assistant Examiner*—Frank Wilkens, III

[57] ABSTRACT

This invention introduces a new unit for suctioning, injection and disposing of different fluids into and from the body of a human being by a special syringe which has a system that allows a fewer buttons or three way stop cocks to be used. This unit will be smaller than similar units and easier to be handled, and will allow a better observation of the intra-cardiac pressure of the patient to be done as well. Also this unit allows a push buttons to be used instead of use of three-way stop cock to avoid rotational motion of hands which some people do not like it.

20 Claims, 8 Drawing Sheets

SUCTION AND INJECTION SYSTEM

BACKGROUND OF THE INVENTION

This invention deals with units for injecting different materials by a syringe and/or with use of manifolds and similar things and particularly during cardiac catheterization and related procedures. Commonly at the present time this is done by connecting a manifold which has a number of three-way stopcocks on it in order to direct one particular solution to a particular route. And commonly this consists of three three-way stopcocks which are arranged in a series to make the manifolds and then such a manifold is connected to the tip of a syringe. However in the experience of this inventor the use of three-day stopcocks is hard and problematic; it causes significant discomfort in some hands and fingers, even pain if it has to be done in a hurry and quickly without using time and care, which are hard to find in these times. Rotation of a three-day stopcock also needs significant work and full functioning hands which increases handling and is a kind of extra work that causes discomfort and tiredness. So a better alternative will make some users happier. This inventor therefore introduces units that have less numbers of buttons to be used and also allow a pressure button to be used instead of a three-day stopcock.

SUMMARY OF THE INVENTION

This invention introduces special types of injection syringes for suctioning and injecting multiple solutions or medications alternatively to a particular place for different purposes. During cardiac catheterization this is a common procedure, and instead of an uncomfortable technique, this method uses a particular syringe which has a system that will do the job of a syringe connected to a manifold easily, quickly and with less work.

DETAILED DESCRIPTION

Figure 1:
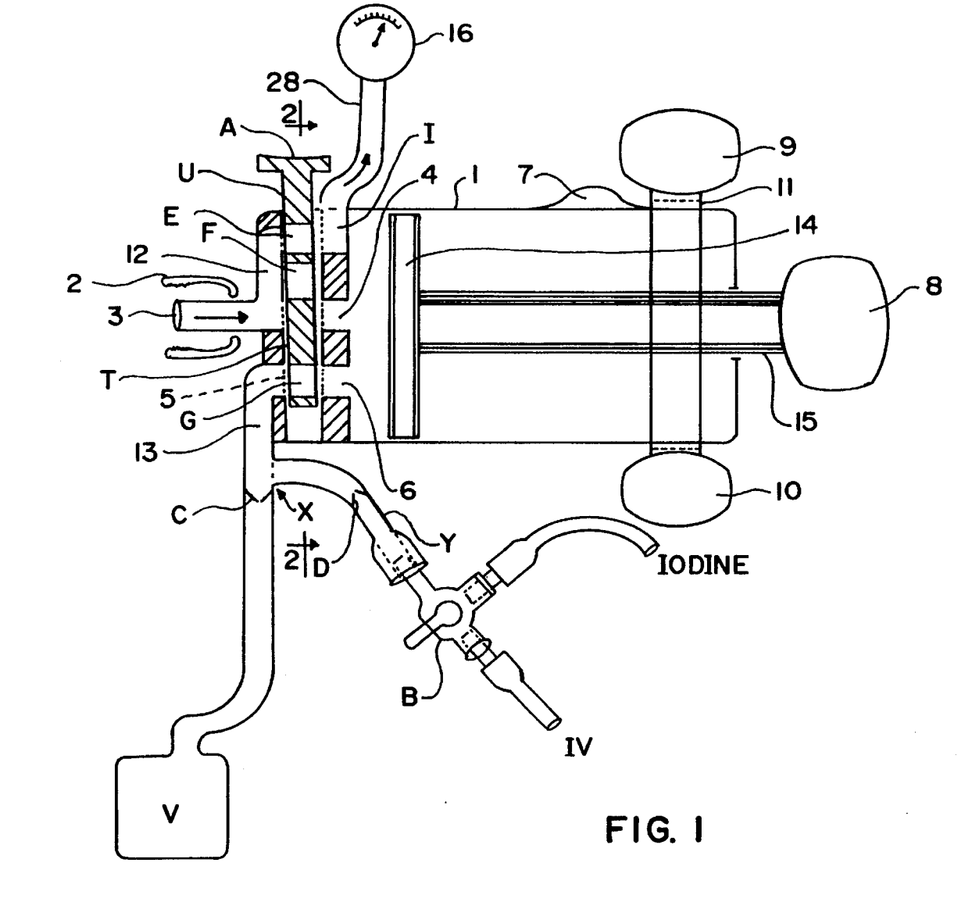
FIG. 1 shows a general view of my injector.
Figure 7:
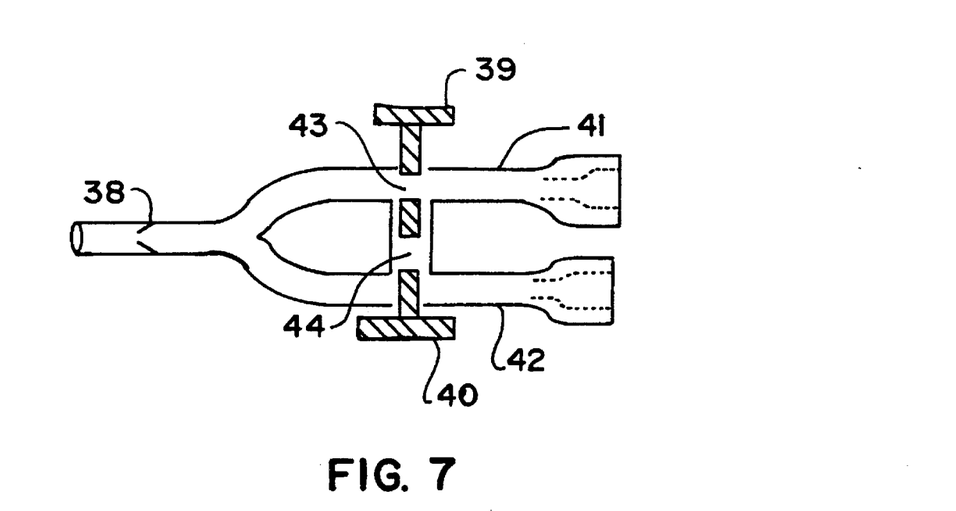
FIG. 7 is a cross section of a valve system.

FIG. 1 is a general view of my injector with a syringe body 1 shown intentionally large in order to allow the details to be seen. However in practice, it will be made smaller, about the size of a 10–11 ml syringe. This syringe has a front part with a tip 3 and a cover 2 to allow connection to a catheter. Cover 2 is similar to a commonly used rotating adaptor to allow the rotation of the catheter to occur easily. This unit has a button A that will stand in the approximate position shown in this Figure. This button will have rounded edges so as not to hurt the fingers and a series of raised lines or spots in its top surface to give an easy grip. When this unit is in the FIG. 1 position, the blood from the catheter will be communicated to a pressure monitor symbolized by a gauge 16 so that when the unit is not being operated, a patient's blood pressure can be monitored continuously. In this initial position, a waste bag V is connected to the syringe through a tube 13 having a one-way valve C which allows fluid to go into the bag but not in the reverse direction. The waste bag is open to the inside of the syringe by the route marked at 5, G and 6. This connection allows injection of waste materials to be done through this route when the syringe is in a waste injecting mode to empty its waste contents. In some particular models, such as the one shown here, a common tube of the IV and Iodine solution is also connected to tube 13 at point X before the connection of this tube to the syringe. In this model the common connection tubing of IV and Iodine solution has a one-way valve D as well. This is to allow the suctioning of the material from the IV or the Iodine bags to occur but not to allow the material from inside of the syringe to go into the IV or Iodine bag during the injection. A three-way stopcock B (whose handle is intentionally shown in this way to prevent crowding the picture), or in fact any other similar valve such as the one shown in FIG. 7, is used to allow an alternative connection of the IV or the Iodine to be made. Alternatively a female type IV ending may be placed here to allow connection of a regular three-way stopcock (as shown here) to be made. In this figure the body or the extension of button A has a series of specially placed openings E, F, and G to form what may be considered a pushbutton operated slide valve. These openings are to play special roles. For example, in the FIG. 1 position it allows the blood (which comes from a catheter connected to tip 3) to be connected through the route marked at opening 12, to opening E, and opening I in the direction of the arrow toward the pressure monitor symbolized at 16. In this position the inner opening of tip 3 is blocked from an opening 4 within syringe body 1 by the solid part of the body of the slide valve. Importantly however, the tube 13 from the waste bag is connected to the syringe interior by route 5, G and 6, and the common tube of IV and Iodine marked at Y is also connected to the syringe via the same route. Now if button A is fully pressed down as in FIG. 2, then the solid part U of the body of this piece will block the connection of the tube 12 to the opening I, and the pressure monitoring no longer occurs. Then the opening F will be placed between the inner opening of tip 3 and the opening 4. This will allow the syringe to suction blood from the catheter (which is connected to the tip 3). At this position then the solid part T of the body will block the connection between 5 and 6. This will prevent the IV or the Iodine from being suctioned inside the syringe when the plunger is being pulled out to operate the syringe in a suction mode. Also in the FIG. 2 position, fluid inside the syringe will be injected into the waste bag if the plunger, is being pushed in. This will allow a very proper functioning to occur. Importantly, the one-way valves placed at C and D may be made to require some resistance to opening in order to prevent the IV from going into the waste bag. In some models, other kinds of valves, such as three-way stopcocks, may be also added to this area to allow them to be closed as well.

Also of interest is the piece containing finger holes 9 and 10 which allows the fingers of the user to fit in for pressing the plunger. This piece has a base 11 that can rotate around the body of the syringe to allow its position to be altered in order to make it comfortable for the user. The head of the syringe plunger is 8. The Iodine line is marked Iodine, and the IV fluid line is marked IV. The piston of the plunger is 14 and its shaft is 15. Numeral 28 is a connecting tube between the syringe and pressure monitoring syste, or transducer, and importantly this tube may alternatively take a different route and direction, either outside or inside the wall of the syringe.

Importantly this unit will have color coding to allow easy recognition and handling. For example, the opening for the tubing for the Iodine may be colored yellow, the opening for the IV line colored blue, and the opening for the waste bag colored red. Also the tubing itself may have a series of spots or lines of different shapes and color, which would not prevent seeing the inside fluid, but still would allow the nature of the material inside it to be recognized by that color coding.

Figure 2:
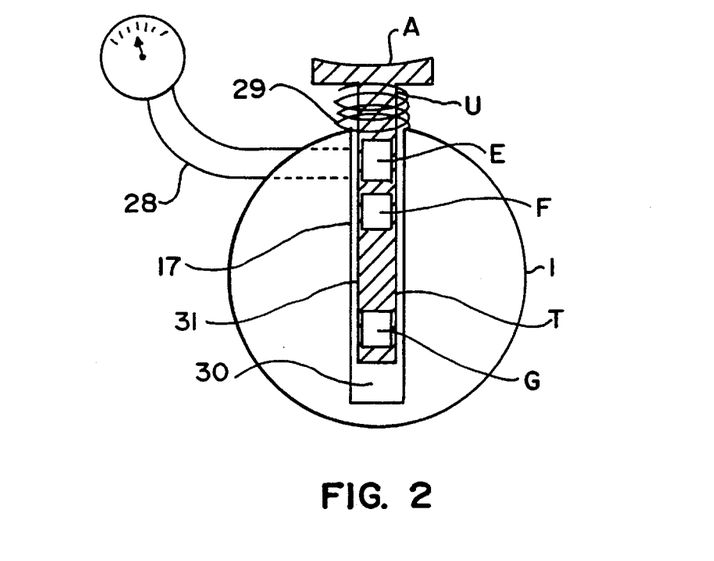
FIG. 2 is a transverse cross section in the direction of arrows 2—2 in FIG. 1.

FIG. 2 shows the unit of the previous figure with the valve body 31 extending down inside the matching tube 17. Openings E, F, and G are designed to match the openings of the tube 17 in certain positions in front of different parts as shown in FIG. 1. The spring 29 is to push the valve up after the pressure is released on button A. Another spring (not shown) may also be placed in the space 30.

Figure 3:
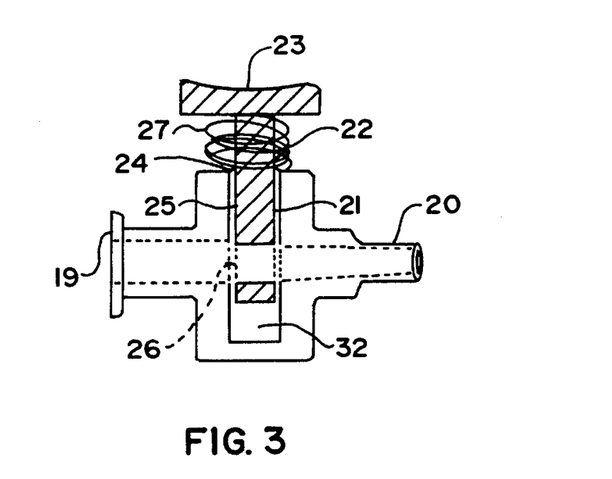
FIG. 3 shows a valve, partly in cross section.
Figure 4:
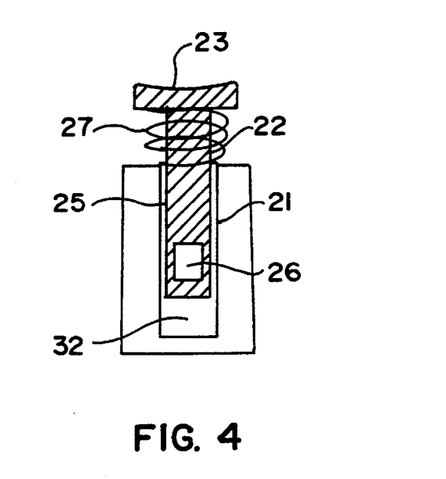
FIG. 4 is a transverse cross section in the direction of arrows 4—4 in FIG. 3.

FIGS. 3 and 4 show a model of valve that uses pressure rather than a twisting mechanism to close the circulation of the fluid (may open a fluid circulation or redirect it). In this figure the female connection end is shown at 19 and the male end at 20. The opening 21 is a space in which a matching piece 25 slides with pressure. These parts have openings that will match and allow circulation of the fluid to occur through these openings. However with pressing the button 23, the opening 26 will move down to close the circulation of the fluid. The spring 27 will make the button move up after the downward pressure is released. The tight edge 24 is to prevent fluid leakage. Alternatively the spring may be placed in a space 32 to push the piece 25 higher. The proper engineering will be used to prevent leakage of fluids. Pieces of latex or similar material and collars may also be used for this purpose.

Figure 5:
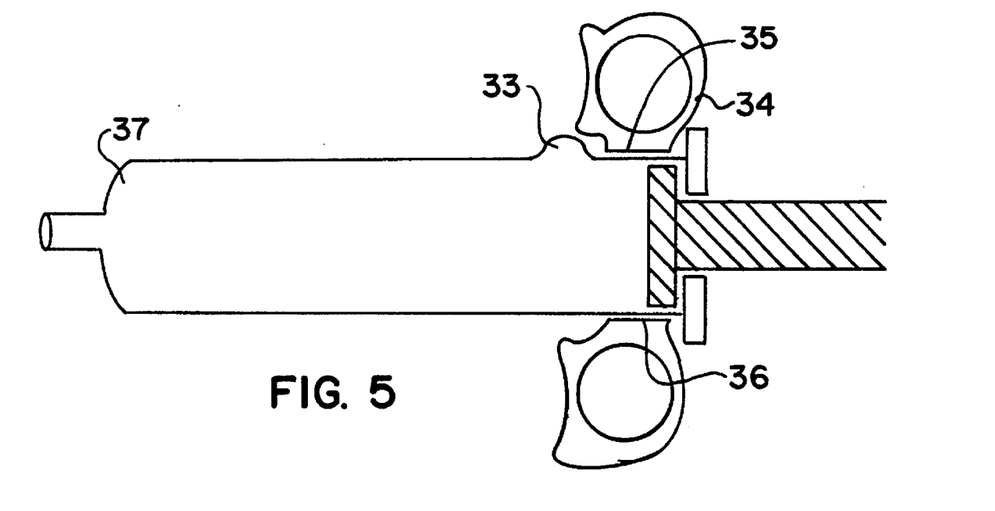
FIG. 5 is a longitudinal cross section through a syringe.
Figure 6:
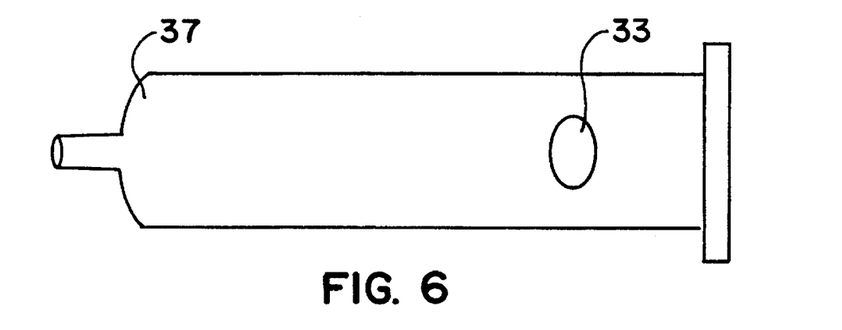
FIG. 6 is a view taken in the direction of arrows 6—6 in FIG. 5 with certain portions omitted.

FIGS. 5 and 6 show a syringe in order to illustrate a few important features: one is the air space shown at 37 which attracts and holds small air bubbles, especially with the tip of the syringe held down and the base in a higher position. Also the doming shape of the front wall of this syringe, shown at 37, is intentional to prevent all the fluid inside the syringe from being injected, again in order to prevent small air bubbles from being injected into the patient during a forced injection. The other point is to show the shape of the handle piece shown at 34 that will allow the fingers to be inserted and to be comfortable when squeezing the plunger. Importantly this piece is shown to be adjustable and to rotate around the outer surface of the syringe so that its position can be changed as desired. The base of these finger holes is shown at 35 and 36 and is separate from the syringe's body to allow rotation to occur and to be set in an ideal position. The finger holes will be made to be comfortable with edges that are curved in order not to hurt the hands and fingers. The buttons and the syringes will be made the same way as well, to be nicely curved and soft.

FIG. 7 shows a valve system that may be used with this unit to allow the IV solution or the Iodine to be selected for injection. This unit is like a three-way stopcock except it uses pressure in one direction to open a valve, rather than the rotational motion which is used in a three-way stopcock. It is believed that this will be a better means for some users. In this figure the valve is placed in the center in the way of two tubings shown at 41, 42. The buttons of the valve shown at 39–40 will allow one line to be open and the circulation of the fluid to occur, which in this case is the line 41. However, if the button 39 is pressed all the way into this valve, then the opening of the line 41 will be closed and the opening 44 will allow the circulation of the fluid in line 42 to occur. The optional one-way valve shown at 38 will make this unit a special unit to allow a directional circulation to occur. Naturally the construction of such unit can be modified to have different shapes, sizes and configurations. This unit may be used instead of the combination of three-way stopcock B and one-way valve D from FIG. 1. Importantly this unit can be modified and shaped to be placed outside of the body of syringe 1 as in FIG. 8. This connection may be made adjustable to allow the position of the unit to be changed for ease of use, and it can also be made to be a temporary connection so that it can be separated. For example, this unit may have a band to allow it to be kept around the syringe and tightened in the right spot; also many other means may be used for such purpose. This unit will be also color coded for easy recognition and handling. For example, tubing 41 and its connected opening may be colored yellow as well as button 39 to indicate that when it is pressed the running fluid is Iodine. The bag of the iodine may be colored in the same way as well, and the tubing may have writing on it to say "Iodine" repeatedly. Likewise tubing 42, its connected female opening, and button 40 may be colored blue to indicate that when button 40 is pressed, the running fluid is the IV fluid. Again the bag of the IV solution may be colored in the same way as well, and the tubing may have writing on it to say "IV solution" repeatedly for easy recognition. The tubing themselves may also have lines or spots of the same coloring to allow the recognition of the fluid inside. A small window may be also made in the front of the body of this piece so that by moving the middle part (the middle part needs to have the different colors in side of its center line), the window properly shows the same color inside which is open to flow. This is not shown in this figure but is easily understandable.

Figure 8:
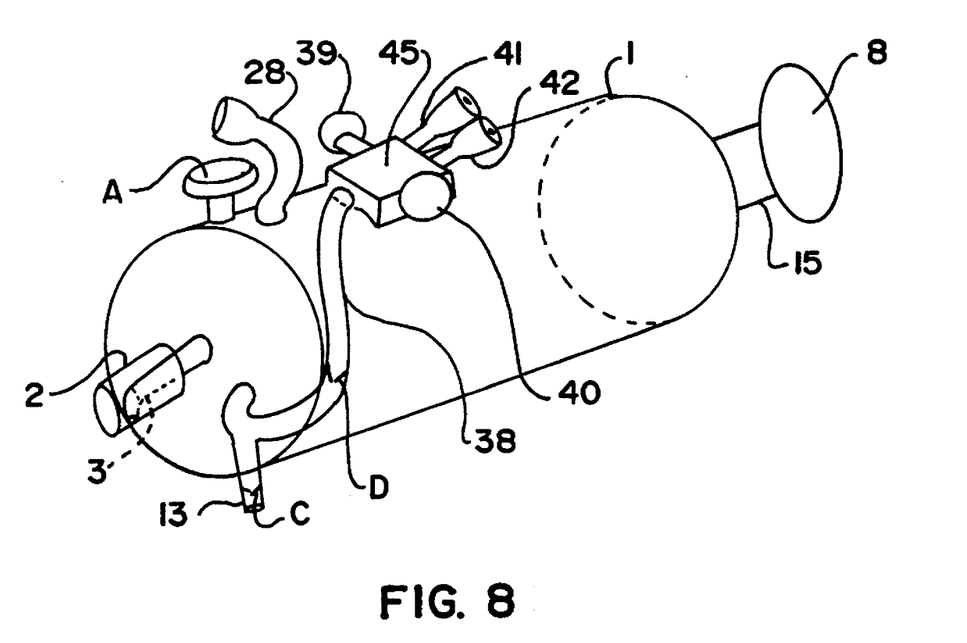
FIG. 8 is a perspective view that shows a unit with the valve system of FIG. 7.

FIG. 8 shows a unit similar to the one shown in FIG. 1, but modified by having a piece similar to the one shown in FIG. 7 placed on its top surface so that it will allow connection of the IV and Iodine solution to it. In this unit the body of the valve is marked at 45. The female type openings 41, 42 that can be also color coded to indicate the materials connected to it are also shown. The outgoing tube from this valve is shown at 38. It will connect to the end piece 13 which is to be connected to the waste bag. Importantly this piece may have a one-way valve inside it that will function like the one-way valve C from FIG. 1. Alternatively this one-way valve may be placed in the tube of the waste bag. The one-way valve D is also shown. The buttons 40 and 39 are conveniently located to be pressed when desired. Importantly this piece can be made in some models to be adjustable so that first it can be temporarily connected to the syringe when desired, and second when in place, its position can be adjusted by moving it to the sides, by rotating it, etc.

This temporary connection may be done by the following methods:

1. By having the piece placed in a cradle made for it on the outside of the syringe wall so that the piece will sit and be held in place by a releasable snap. This allows its use either on the surface of the syringe, or free from it.

2. By having the piece placed on or attached to a band by different means so that this band can go around the syringe and be tightened by a snap, adhesives, Velcro™ or any other similar means. This method will allow the place and position of such units to be easily decided.

3. This connection can be permanent so that the whole unit is constructed to be part of the syringe's wall and easily utilized. This can be done in different parts or areas of the syringe to give different models and alternatives. In this case, the connection pieces may be in shape of female connection IV tubing, or they may have tubing that is long and ends with female ends.

4. These pieces may be made to be totally separate with only the end of the tube 38 coming and being connected to the syringe at one point. This tube may have the one-way valve D, or importantly the one-way valve may be made to be in the part of the tube which is fixed to the syringe, or else part of its wall.

5. Importantly the valve 45 may be chosen to be a three-way stopcock. It can be separate from the syringe or can be placed in different places and by different means on the syringe. Its shape may be modified as well.

6. Importantly the three-way stopcock mentioned in 5 above may also be modified to have the one-way valve D in its end piece to make a compact unit, ready to be used.

7. The female endings of such unit may be made in the shape of a funnel so that it will make the connection easier. They may also have pieces of spring or plastic hooks that will make the connection sturdy, similar to the models shown in my previous application Ser. No. 08/172,754 filed Dec. 14, 1993, These are shown at FIGS. 11–17.

Importantly in order to prevent fatigue of the hands in cases when some people have problems with injections, then this syringe may be modified to be mounted in a lever on a plastic base to allow the lever system to be utilized for injection. The other components of this unit may be also modified to make a comfortable handy unit.

Also in some models, pressure injectors may be utilized to make this job easier. It is also possible to use advanced electronics components and computer chips, and electrically powered pieces and components, to make a unit where the valves would be controlled by that system automatically so that by pressing a button, one type of circulation is set for use. For example, the injection mode for the coronaries can be ready for use; suctioning of the catheter can be done, etc.; or at least some parts of this unit can be electronic.

Figure 9:
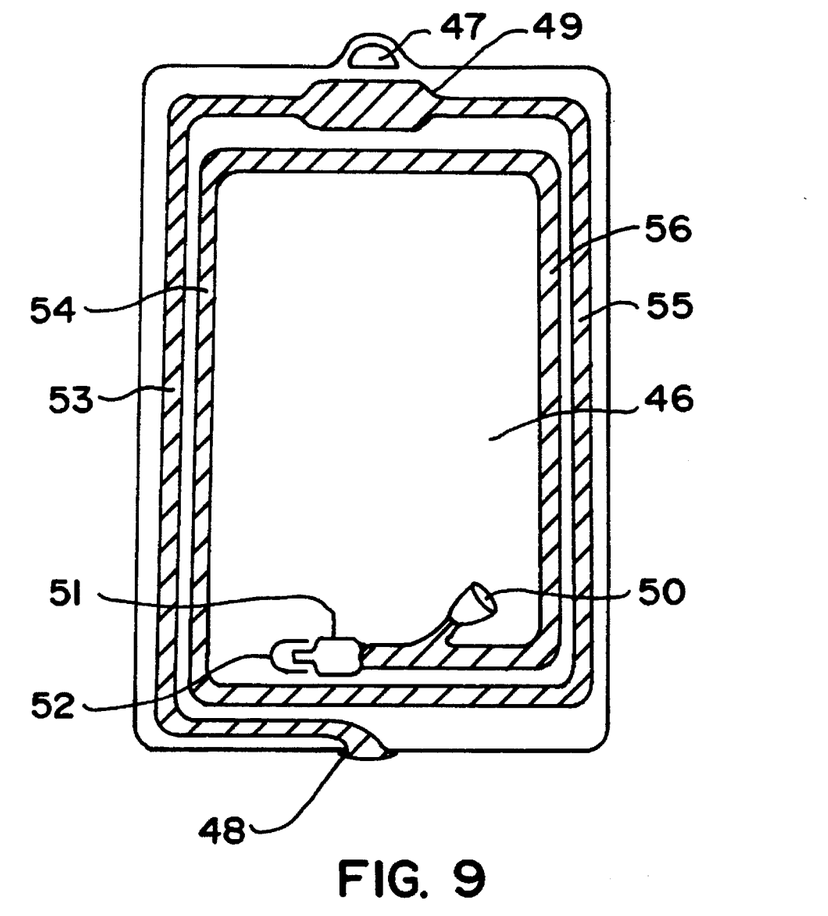
FIG. 9 shows a special IV bag that will be used with this unit.
Figure 10:
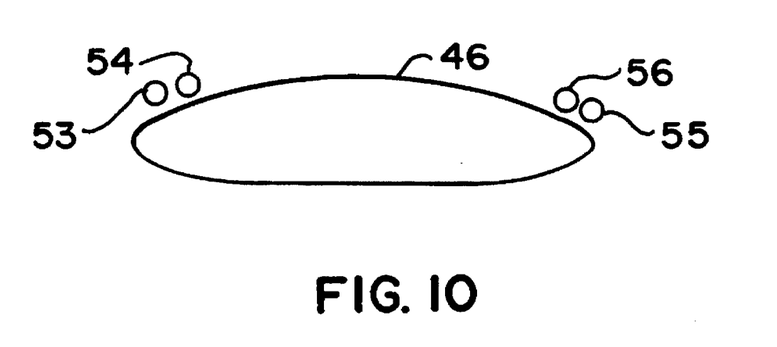
FIG. 10 is a schematic cross cut view of the IV bag shown in previous figure of 9.
Figures 11, 12, 13, 14, 15:
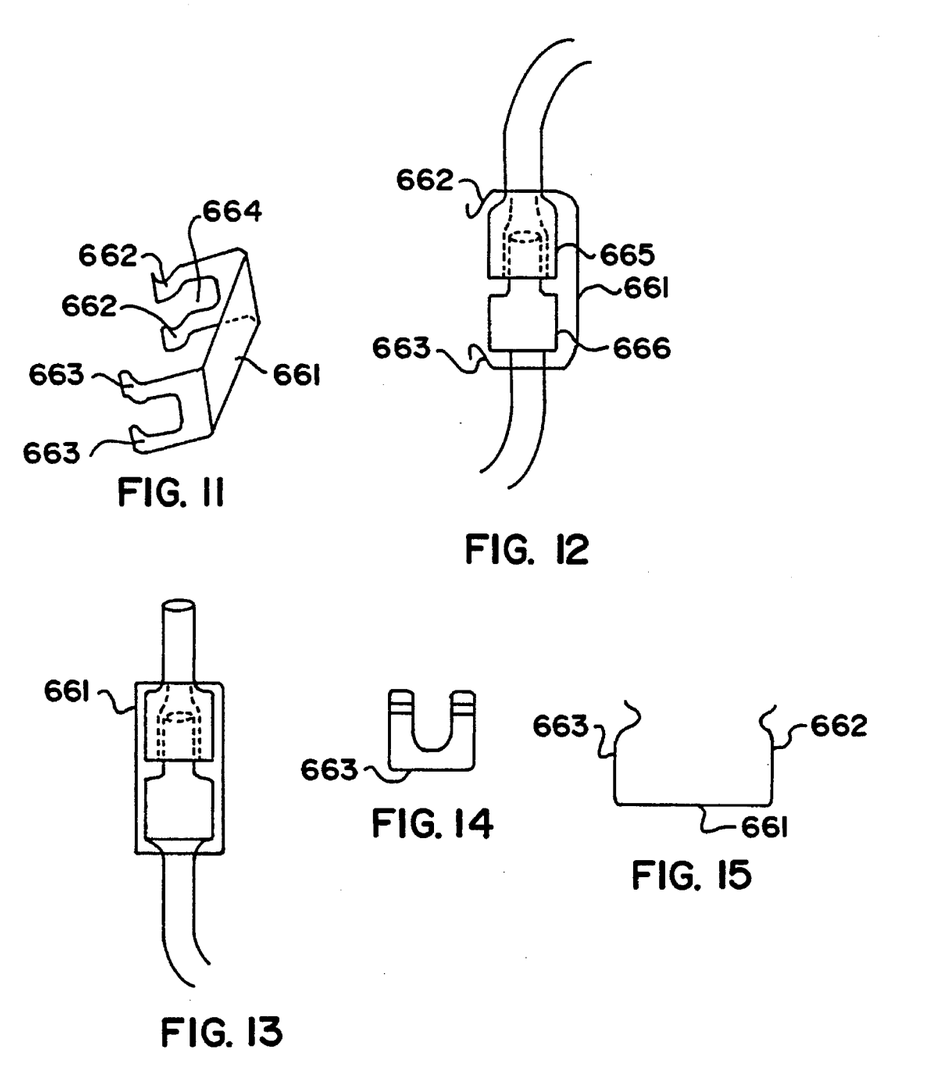
FIG. 11 is a perspective view of a clip for holding tube fittings engaged.
FIG. 12 is a plan view showing usage of the clip of FIG. 11.
FIG. 13 is a right side view of FIG. 12.
FIG. 14 is an end view of the clip by itself.
FIG. 15 is a right side view of FIG. 14.
Figure 16:
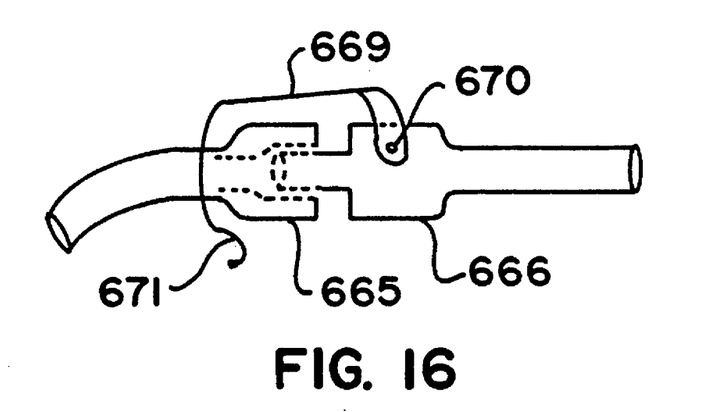
FIG. 16 is a plan view of a modified form of clip.
Figure 17:
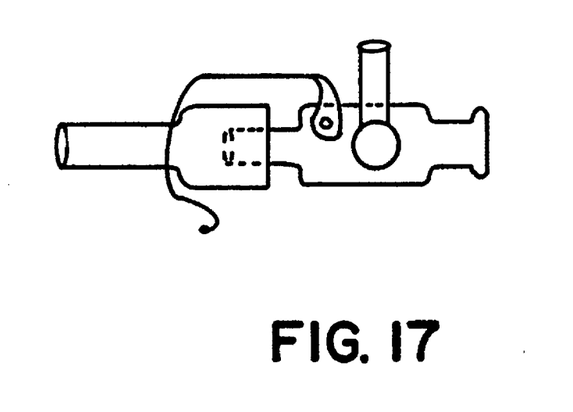
FIG. 17 is a plan view of another modified form.

FIGS. 9 and 10 show a special IV bag that will be used with this unit. The body of this IV bag is shown at 46, the hanging area of this unit at 47, and the connected point of the tubing to the bag at 48. Then the tubing continues its way around the bag at 53 and has an expanded space shown at 49 that is to allow the dripping of the drops to be seen. The tube continues in the right side of this figure at 55, then in the left side at 54, and it continues at 56 in the right side again, to come and end at 51 with a standard male IV ending covered at 52. The opening 50 is a funnel shaped unit which has a membrane from latex or similar material for injection of materials. This part is specially designed in this form to prevent the accidental puncturing of the fingers that hold the part for injection. Importantly this can be used in openings of the medication bottles and other IV connections as well.

BEST MODE OF OPERATION

During certain procedures such as cardiac catheterization, there is a need to suction blood and/or different fluids and medications from the body, a container or a space, and to inject fluid to the other side repeatedly. This involves handling many different materials such as blood, IV fluids, Renographine or other Iodine solutions, etc. Procedure fluids are to be injected into the body by a catheter that is connected to a syringe, and the waste materials are injected into a waste bag. At present this is commonly done by combinations of a syringe and a manifold. The syringe is connected to the manifold which has a raw of three-way stopcocks in series. They can be opened or closed with a special plan to allow the circulation of the fluids to be done in a particular direction and the materials to be injected into a certain side. However in the experience of this inventor, this is a very difficult unit to handle and a long, uncomfortable one as well. Three-way stopcocks are hard to handle, and their rotation causes a significant discomfort in some people, and even pain in the fingers, if it has to be done quickly without time to pay significant attention to prevent the pain. Rotation of a three-way stopcock involves a significant amount of work, and at times even needs a full functioning pair of hands; one to hold the base and the other one to twist, which is hard, causes discomfort, and is a waste of time. If a better alternative were present, such discomfort and waste could be happily avoided. Learning how to handle three three-way stopcocks in a manifold is difficult as well, and in general using one unit for a job is better than using two units. Therefore the inventor introduces his present unit which has some advantages as follows:

First, this is a single, combined unit which allows all the jobs to be done easily.

Second, it has the advantage that the total numbers of buttons are reduced and only two are used.

Third, this unit will primarily use pushbuttons rather than rotational types such as three-way stopcocks. The inventor believes his unit is better.

Fourth, this unit will allow a rapid and almost automatic connection of the catheter from the patient to the transducer to be made for monitoring blood pressure. Such monitoring is a very important factor in these procedures.

Fifth, this unit has a significant versatility. It will allow different models to be made, and the button for switching between the IV and Iodine solution, to be placed in any place that the performer wishes.

Sixth, the syringe of this unit will have a space in its rear top surface to entrap and hold the small bubbles of the air that are usually created and present inside the syringe and that may, on occasions, be injected inside the coronary or circulation, damage in important areas of the body.

Seventh, the unit will be clear and transparent in the areas that are needed to allow observation of the motion of air bubbles.

This unit will be made from a combination of the following units:

A. It will use special valves (a simple sample of which is shown in FIGS. 3 and 4) that open or close with pressure of the finger. Then a spring or a pressure mechanism, such as fluid pressure, etc., will cause the valve to return to its original position. This eliminates the need for rotation of a three-way stopcock, which is believed to be hard at least for certain people.

B. It will use one or more one-way valves in order to direct the circulation in one particular way and prevent reverse movement.

C. This unit will use a rotating adaptor connection tip to allow the catheter connection to the syringe to be done easily and the catheter to be rotated easily.

D. The handle or the place for insertion of the fingers for injection will be adjustable and rotate so that the plane of this piece compared to the axis of the syringe can be changed. This is to enable the user to find a position which is most comfortable for him. They will be made to be comfortable by having edges that are curved in order not to hurt the hands and the fingers. The buttons and the syringes will be made the same way as well, to be nicely curved and soft; this will also include the base of the plunger as well.

E. This unit may be made to allow the control ends of IV and Iodine solution, or different tubings, to be connected to its surface in an easy place for easy control.

F. This unit may be made to have the tubings for the IV and Iodine solution connected to its ends so that they will be ready to be inserted into the bags to eliminate some of these jobs.

G. The system of color coding will be utilized to make decision making easier and faster.

I. The unit may have the IV bags as well as the Iodine bags connected to it by the proper tubing so that they will be ready for use, eliminating the job of connecting a tubing to the IV bags and expediting the whole process.

J. The unit will have the waste bag connected to it to decrease the job, or it may have the opening for the bag to be connected. The waste bag will be color coded as well.

As specified above in some models, the unit will have the IV tubings connected to the proper parts of the unit so that the unit will have the tubes ready for connection to the main IV bag, the Iodine bag and the waste bag. The unit will only need the tubes to be stuck into the right opening of the bags.

Also importantly, in some other models, this unit will have the tubings connected to the proper parts of this unit, to the related IV bag, to the Iodine bag, and to the waste bag so that the unit will only need to be hung on a place in order to function. These bags may be made in a shape similar to the one shown in FIGS. 9 and 10 so that they can be packed easily. In this kind, the tubing can be placed nicely around the plastic bag, then the bags packed one next to or over the other, with the syringe next to them or connected to them. The unit will be packed sterile to be ready for use. This will save some time which will add up finally to be a significant saving of important time in the cardiac catheterization lab.

Importantly this unit may be also made to have the female ends of it to be specially shaped like a funnel shape in order to allow easy connection with much lesser chance of accidents as well.

How this unit will function will be explained in the following way:

First, the unit will be connected to the IV and Iodine by the proper tubing and rotation of the three-way stopcock B. Then the syringe can be flushed and filled with IV fluid. This is easy in the position shown in FIG. 1. The front opening which is at the base of the tip 3 is closed by solid T part of the slide valve, and the IV fluid can flow through the three-way stopcock B and the one-way valve D. The one-way valve D will allow the IV fluid to be suctioned inside the syringe and then to be flushed out easily by forcing the plunger of the syringe forward to inject the blood inside the waste bag shown at V in FIG. 1 through the route comprising 6, G, 5, tube 13 and one-way valve C. Importantly during the injection, this fluid cannot go inside the IV since the one-way valve D will prevent it. Also importantly during suctioning of the fluids from the IV and Iodine solution tubings, the one-way valve C will prevent the material from the waste bag from being suctioned inside the syringe, and so this whole function will be nicely done. Alternatively, instead of the IV fluid, the Iodine can be connected to the syringe by proper positioning of a special valve or three-way stopcock B to allow the tubings and the syringe to be filled with Iodine.

Importantly the one-way valves placed in the C point and D as well may be made to need some resistance to open to prevent the IV from going into the waste bag. In some models other kinds of valves, such as three-way stopcocks, may be also added to this area to allow them to be closed as well.

Then the transducer which is symbolically shown by the gauge 16 in FIG. 1 can be flushed separately by another syringe and the use of a three-way stopcock usually connected to this tubing.

Figure 1A:
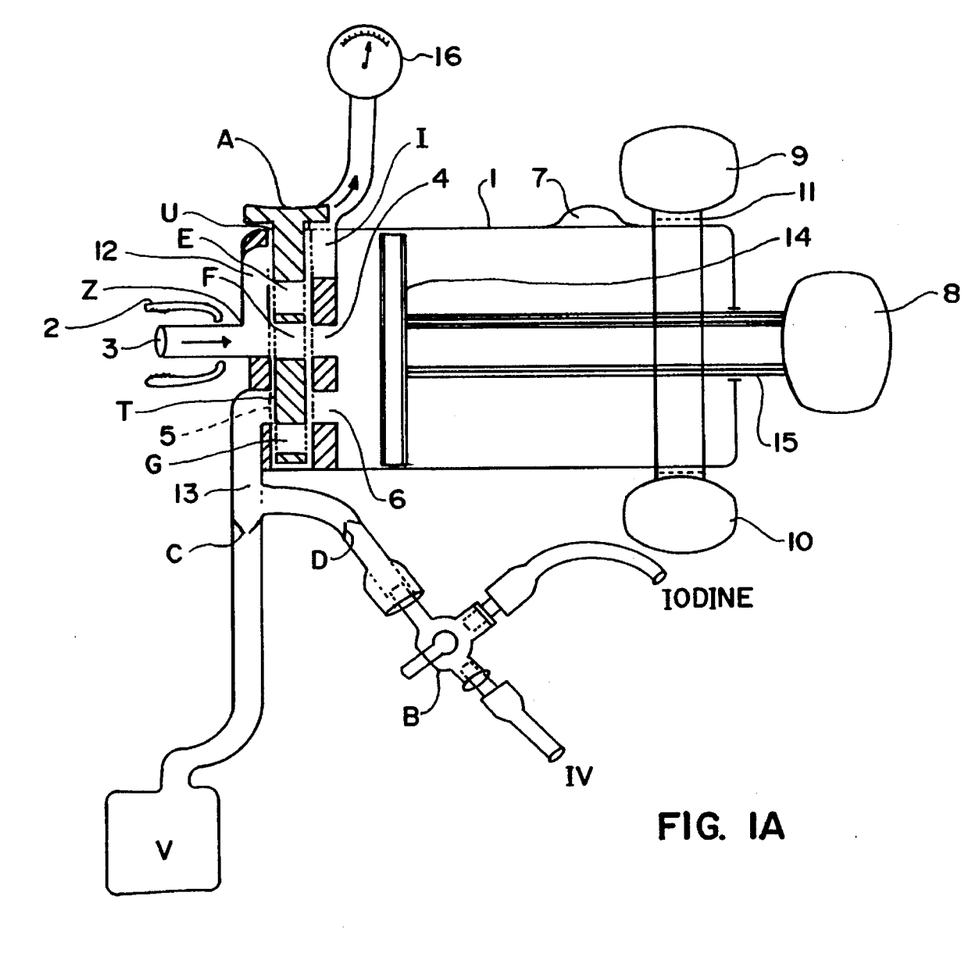
FIG. 1A shows a different operating position of my injector.

After the angiography, the catheter is placed inside the body of the patient and is connected to the front of the syringe at point 3; then for flushing the catheter and other jobs, the button A of the slide valve will be pressed down as shown in FIG. 1A to do the following jobs simultaneously:

1. To connect the inner lumen of the catheter to the inner lumen of the syringe through the openings 3, 12 and 4.

2. To close the route to transducer 16 by having the solid piece U of the valve stand between the tube 12 and route I so that the injected material cannot be injected inside the transducer.

3. To close the opening 5 and 6 by the solid piece T which will prevent the injected material from being flushed to inside the waste bag.

4. At the end when the button A is released, spring 29, or a similar means, will push the valve back to its original position shown in FIG. 1.

Thus, when button A is pressed, the blood can be suctioned into the syringe from the catheter and with release of button A, it can be injected easily inside the waste bag. When the button A is not pressed the IV solution can be suctioned from the IV bag (when the three-way stopcock is in proper position) to fill the syringe and then easily injected into the waste bag without need to do any further change or job. This can be done as frequently as desired to clean the syringe. Also when button A is not pressed, the saline can be suctioned from the IV bag to fill the syringe, and with pressing button A, it can be flushed into the catheter to flush it. This process can be repeated as desired.

At this time usually, the system is ready to allow injection into the coronaries. For this purpose, the three-way stopcock B will be positioned properly to connect the Iodine to the syringe. In this position, first the Iodine will be suctioned easily inside the syringe and the small bubbles of the air will be released to the waste bag, the few remaining will be collected inside the air space, and then the system will be ready for use. At this point button A will be pressed, and then after suctioning a small amount of the blood from the catheter to clear possible air, the Iodine will be injected into the catheter while button A is being pressed. After injection of the Iodine (Renographine) is over, button A will be released to connect the catheter to the pressure monitor for observation of the pressure of the patient. Importantly after this initial injection, further injections of Iodine can be continued easily by suctioning the Iodine from the bag without a need to do any further job and to be injected to the catheter over and over. This process can be repeated or altered as desired.

The function of flushing the pressure transducer may be done with some different plans; for example, it may be done by use of a three-way stopcock that is commonly connected to these units, or there will be a three-way stopcock connected to the point close to point I. Or in some models a valve like a mini-door may be placed at point Z (FIG. 1A) to prevent the blood from the catheter from moving into the tubing or passage 12 and to the transducer. Also it is possible to have a valve or a three-way stopcock placed in the position along the end piece 3, or in tubing, or passage 12, to allow flushing of the system to be done through that way. Other alternatives may be chosen by having such basic options in mind if it became necessary to allow the connection between the syringe and the tubing of the transducer to have an opening and a valve so that another syringe and three-way stopcock can be connected for this purpose.

Also importantly the opening of the waste bag and the IV Iodine line into the syringe may be separate to avoid any problem of the IV fluid going into the waste bag. In such a case operation of button A will close these openings simultaneously, but separately, and their opening into the syringe may be common or separate.

Importantly the slide valve may use a different mechanism as well in order to make it more comfortable for use; for example, it is possible to make it maintain its position after button A is pressed and to be released with a second push or pressing to button A. Or a second button can do this job. This valve may be even made to use a rotational motion for its job but the rotation to be done with use of a larger circle so that the motion of rotation will be like a pressure rather than the rotation around a smaller circle.

Also importantly the entrance of the openings into the syringe can be in different spots as well to allow smaller units to be made and/or the manufacturing or handling of the unit to be easier or better. Also extra valves of any kind may be used along the tubings to allow better control.

Importantly the tip 3 of the syringe does not need to be necessarily in the center and it can be placed in the rim or even in some models in the sides as well. And also it should be noted that the connection area/point or port of the IV Iodine, or the waste bag, to the syringe may only be made to be a male or female connection port, or end, similar to commonly used IV connection ends, and not a long tube.

Importantly special and different valves may be made and used with these units. A compact model of a valve shown in FIG. 7 can be used in any kind of IV connections to satisfy certain users who do not like to use rotational motion due to the condition of their hands. A model of this valve may have the one-way valve in its construction as well.

Also importantly these connection ports may have the one-way valves D and C incorporated inside themselves so that the waste bag and the IV Iodine lines would not need to have the one-way valves.

The connection port of the transducer to the syringe may also only be made to be a male or female connection port, or end, as mentioned, and not a long tube. This spot may have a three-way stopcock in it to accept one as well.

Importantly the general shape, the size, the thickness, the relations of different parts and their relative sizes, the nature of the valves, the coloring, the material used in manufacturing of this unit, and the other important characteristics of this unit may vary from one model to another. The place of the ports on the surface of the syringe may be different than the actual entrance of that part into the body of the syringe to allow better handling. For example, the port for the IV Iodine connection may be on the left side of the unit, in the top, or in the side, but to be connected to the inner syringe from the front. This is to allow easy handling and the placement of the valve in the way to be done as well.

The inventor believes that the set up and the plan of this unit is the important part of this invention, and he believes that importantly, the proper engineering techniques can be used to make this basic units in different shapes and models to do this job in the best way. He believes that with use of available engineering techniques and skills it will be possible to make the valves to avoid leakage and to be handled comfortably; pieces of latex or similar material will be used in areas where leakage of the fluid occurs. The valves may be also caged inside a latex cover to prevent leakage of fluid outside, and even in such cases, the latex may go all around the valve area.

Although this unit is basically made for cardiac use, it is however possible to make modified units to be used in similar jobs as well.

I claim:

1. A suctioning and injecting system for use with a catheter during a catheterization procedure, said system comprising:

1) a syringe having a barrel and a plunger for suctioning fluid into the barrel during a suction stroke of the plunger and for injecting fluid from the barrel during an injecting stroke of the plunger;

2) first port means for placing the system in fluid communication with such a catheter;

3) a fluid source means that provides one or more fluids during the course of such a procedure;

4) a fluid waste disposal means for receiving waste fluid during the course of such a procedure;

5) second port means for placing the system in fluid communication both with said fluid source means and with said fluid waste disposal means; and 6) means, including slide valve means that is interposed between said first and second port means and said barrel and that is selectively positionable to first and second selected positions, for selectively respectively communicating said first and second port means with said barrel such that in the second selected position, said slide valve means communicates said second port means to said barrel while blocking communication of said first port means with said barrel to allow fluid from said fluid source means to be suctioned into said barrel during a suction stroke of said plunger and waste fluid previously suctioned into said barrel from such a catheter through said first port means during a suction stroke of said plunger while said slide valve means was in the first selected position, to be injected from said barrel into said fluid waste disposal means during an injecting stroke of said plunger, and such that in the first selected position, said slide valve means blocks communication of said second port means with said barrel while communicating said first port means with said barrel to allow waste fluid from such a catheter to be suctioned through said first port means into said barrel during a suction stroke of said plunger and fluid previously suctioned into said barrel from said fluid source means through said second port means during a suction stroke of said plunger while said slide valve means was in the second selected position, to be injected from said barrel through said first port means into such a catheter during an injecting stroke of said plunger.

2. A system as set forth in claim 1 in which check valve means connects said fluid source means and said fluid waste disposal means with said second port means, and in which said check valve means comprises means for allowing fluid to be suctioned from said fluid source means through said slide valve means into said barrel of said syringe during a suction stroke of said plunger, when said slide valve means is in its second selected position, while concurrently preventing waste fluid from said fluid waste disposal means from being suctioned into the barrel along with fluid from said fluid source means, and for allowing fluid that has been suctioned into the barrel to be injected from the barrel through said slide valve means to said fluid waste disposal means during an injecting stroke of said plunger, when said slide valve means is in its second selected position, while concurrently preventing the fluid from being injected into said fluid source means.

3. A system as set forth in claim 2 in which said second port means comprises a single port, said fluid source means and said fluid waste disposal means are in separate fluid branches having common communication with said single port via said check valve means, and said check valve means comprises a respective check valve in each respective fluid branch.

4. A system as set forth in claim 3 in which said fluid source means comprises a first fluid source, a second fluid source, and source selection valve means for selectively placing said first and second fluid sources with the fluid branch that communicates said fluid source means with said single port.

5. A system as set forth in claim 4 in which said source selection valve means comprises its own slide valve means.

6. A system as set forth in claim 1 in which check valve means connects said fluid source means and said fluid waste disposal means with said second port means, and in which said check valve means comprises means for allowing fluid to be suctioned from said fluid source means through said slide valve means into said barrel of said syringe during a suction stroke of said plunger, when said slide valve means is in its second selected position, while concurrently preventing waste fluid from said fluid waste disposal means from being suctioned into the barrel along with fluid from said fluid source means, and for allowing fluid that has been suctioned into the barrel to be injected from the barrel through said slide valve means to said fluid waste disposal means, when said slide valve means is in its second selected position, while concurrently preventing the fluid from being injected into said fluid source means, said fluid source means comprises a first fluid source, a second fluid source, and source selection valve means for selectively placing said first and second fluid sources in communication with the fluid branch that communicates said fluid source means with said second port means, said source selection valve means being disposed between said check valve means and said first and second fluid sources.

7. A suctioning and injecting system for use with a catheter during a catheterization procedure, said system comprising:
  1) a syringe having a barrel and a plunger for suctioning fluid into the barrel during a suction stroke of the plunger and for injecting fluid from the barrel during an injecting stroke of the plunger;
  2) first port means for placing the system in fluid communication with such a catheter;
  3) second port means for placing the system in fluid communication both with a fluid source means that provides one or more fluids that, during the course of such a procedure, are suctioned into the barrel of the syringe and then injected from the barrel and with a fluid waste disposal means into which waste fluid that has been suctioned into the barrel during the course of such a procedure is injected from the barrel; and
  4) means, including slide valve means that is interposed between said first and second port means and said barrel and that is selectively positionable to first and second selected positions for selectively respectively communicating said first and second port means with said barrel such that in the second selected position, said slide valve means communicates said second port means to said barrel while blocking communication of said first port means with said barrel, and in the first selected position, said slide valve means blocks communication of said second port means with said barrel while communicating said first port means with said barrel;
  5) including a third port means that is communicated to said first port means when said slide valve means is in its first selected position.

8. A system as set forth in claim 7 further including a pressure measuring means connected to said third port means for measuring pressure at said first port means as communicated by said slide valve means to said third port means.

9. A suctioning and injecting system for use with a catheter during a catheterization procedure, said system comprising:
  1) a syringe having a barrel and a plunger for suctioning fluid into the barrel during a suction stroke of the plunger and for injecting fluid from the barrel during an injecting stroke of the plunger;
  2) first port means for placing the system in fluid communication with such a catheter;
  3) second port means for placing the system in fluid communication both with a fluid source means that provides one or more fluids that, during the course of such a procedure, are suctioned into the barrel of the syringe and then injected from the barrel and with a fluid waste disposal means into which waste fluid that has been suctioned into the barrel during the course of such a procedure is injected from the barrel; and
  4) means, including slide valve means that is interposed between said first and second port means and said barrel and that is selectively positionable to first and second selected positions for selectively respectively communicating said first and second port means with said barrel such that in the second selected position, said slide valve means communicates said second port means to said barrel while blocking communication of said first port means with said barrel, and in the first selected position, said slide valve means blocks communication of said second port means with said barrel while communicating said first port means with said barrel;
  5) in which said plunger has an external actuator for pushing by a person's thumb, and finger grip means that is disposed on the exterior of the barrel and that is selectively positionable on the barrel for comfortable gripping by a person's fingers.

10. A system as set forth in claim 9 in which said barrel has a small dome protruding from its sidewall providing an internal air pocket at a high elevation inside the barrel to which air bubbles can migrate so that they will not be injected from the barrel, and said finger grip means is axially captured between said small dome and a flange on the barrel proximate the external actuator and is rotatable on the barrel to a desired position of comfort for a person's fingers.

11. A suctioning and injecting system for use with a catheter during a catheterization procedure, said system comprising:

1) a syringe having a barrel and a plunger for suctioning fluid into the barrel during a suction stroke of the plunger and for injecting fluid from the barrel during an injecting stroke of the plunger;

2) first port means for placing the system in fluid communication with such a catheter;

3) second port means for placing the system in fluid communication both with a fluid source means that provides one or more fluids that, during the course of such a procedure, are suctioned into the barrel of the syringe and then injected from the barrel and with a fluid waste disposal means into which waste fluid that has been suctioned into the barrel during the course of such a procedure is injected from the barrel; and 4) means, including slide valve means that is interposed between said first and second port means and said barrel and that is selectively positionable to first and second selected positions for selectively respectively communicating said first and second port means with said barrel such that in the second selected position, said slide valve means communicates said second port means to said barrel while blocking communication of said first port means with said barrel, and in the first selected position, said slide valve means blocks communication of said second port means with said barrel while communicating said first port means with said barrel;

5) in which said barrel has a small dome protruding from it sidewall providing an internal air pocket at a high elevation inside the barrel to which air bubbles can migrate so that they will not be injected from the barrel.

12. A system as set forth in claim 11 in which said first port means is a tip that is contained in an outwardly curved end wall of the barrel that prevent the entire contents of the barrel from being injected to reduce the probability of injecting air into such a catheter.

13. A suctioning and injecting system for use with a catheter during a catheterization procedure, said system comprising:

1) a syringe having a barrel and a plunger for suctioning fluid into the barrel during a suction stroke of the plunger and for injecting fluid from the barrel during an injecting stroke of the plunger;

2) first port means for placing the system in fluid communication with such a catheter;

3) second port means for placing the system in fluid communication both with a fluid source means that provides one or more fluids that, during the course of such a procedure, are suctioned into the barrel of the syringe and then injected from the barrel and with a fluid waste disposal means into which waste fluid that has been suctioned into the barrel during the course of such a procedure is injected from the barrel; and 4) means, including slide valve means that is interposed between said first and second port means and said barrel and that is selectively positionable to first and second selected positions for selectively respectively communicating said first and second port means with said barrel such that in the second selected position, said slide valve means communicates said second port means to said barrel while blocking communication of said first port means with said barrel, and in the first selected position, said slide valve means blocks communication of said second port means with said barrel while communicating said first port means with said barrel;

5) in which said slide valve means is disposed in a valve body that is mounted on the exterior of the sidewall of the barrel.

14. A suctioning and injecting system for use with a catheter during a catheterization procedure, said system comprising:

1) a syringe having a barrel and a plunger for suctioning fluid into the barrel during a suction stroke of the plunger and for injecting fluid from the barrel during an injecting stroke of the plunger;

2) first port means for placing the system in fluid communication with such a catheter;

3) second port means for placing the system in fluid communication both with a fluid source means that provides one or more fluids that, during the course of such a procedure, are suctioned into the barrel of the syringe and then injected from the barrel and with a fluid waste disposal means into which waste fluid that has been suctioned into the barrel during the course of such a procedure is injected from the barrel; and 4) means, including slide valve means that is interposed between said first and second port means and said barrel and that is selectively positionable to first and second selected positions for selectively respectively communicating said first and second port means with said barrel such that in the second selected position, said slide valve means communicates said second port means to said barrel while blocking communication of said first port means with said barrel, and in the first selected position, said slide valve means blocks communication of said second port means with said barrel while communicating said first port means with said barrel;

5) in which said slide valve means comprises an external pushbutton for selectively positioning said slide valve means.

15. A system as set forth in claim 14 including a spring means for returning said slide valve means from said first selected position to said second selected position.

16. A suctioning and injecting system for use with a catheter during a catheterization procedure, said system comprising:

1) a syringe having a barrel and a plunger for suctioning fluid into the barrel during a suction stroke of the plunger and for injecting fluid from the barrel during an injecting stroke of the plunger;

2) first port means for placing the system in fluid communication with such a catheter;

3) second port means for placing the system in fluid communication both with a fluid source means that provides one or more fluids that, during the course of such a procedure, are suctioned into the barrel of the syringe and then injected from the barrel and with a fluid waste disposal means into which waste fluid that has been suctioned into the barrel during the course of such a procedure is injected from the barrel; and 4) means, including slide valve means that is interposed between said first and second port means and said barrel and that is selectively positionable to first and second selected positions for selectively respectively communicating said first and second port means with said barrel such that in the second selected position, said slide valve means communicates said second port means to said barrel while blocking communication of said first port means with said barrel, and in the first selected position, said slide valve means blocks communication of said second port means with said barrel while communicating said first port means with said barrel;

5) in which said first port means is a tip of said syringe barrel, and further including a swivel fitting disposed on said tip for connecting with such a catheter.

17. In a suctioning and injecting system for use with a catheter during a catheterization procedure:

1) a syringe-having a barrel and a plunger for suctioning fluid into the barrel during a suction stroke of the plunger and for injecting fluid from the barrel during an injecting stroke of the plunger;

2) first port means for placing the system in fluid communication with such a catheter;

3) second port means for placing the system in fluid communication both with a fluid source means that provides one or more fluids that, during the course of such a procedure, are auctioned into the barrel of the syringe and then injected from the barrel and with a fluid waste disposal means into which waste fluid that has been suctioned into the barrel during the course of such a procedure is injected from the barrel;

4) selectively settable valve means interposed between said first and second port means and said barrel for selectively communicating said first and second port means with said barrel such that in a first selected setting, said valve means communicates said second port means to said barrel while blocking communication of said first port means with said barrel, and in a second selected setting, said valve means blocks communication of said second port means with said barrel while communicating said first port means with said barrel;

5) said barrel has a small dome protruding from its sidewall providing an internal air pocket at a high elevation inside the barrel to which air bubbles can migrate so that they will not be injected from the barrel; and 6) said first port means is a tip that is contained in an outwardly curved end wall of the barrel whose curvature provides a space inside the barrel that prevents the entire contents of the barrel from being injected to reduce the probability of injecting air into such a catheter.

18. A system as set forth in claim 17 in which said plunger has an external actuator for pushing by a person's thumb, and further including finger grip means that is axially captured between said small dome and a flange on the barrel proximate the external actuator and that is rotatable on the barrel to a desired position of comfort for a person's fingers.

19. A system as set forth in claim 17 in which said first port means is a tip of said syringe barrel, and further including a swivel fitting disposed on said tip for connecting with such a catheter.

20. In a suctioning and injecting system for use with a catheter during a catheterization procedure:

1) a syringe having a barrel and a plunger for suctioning fluid into the barrel during a suction stroke of the plunger and for injecting fluid from the barrel during an injecting stroke of the plunger;

2) first port means for placing the system in fluid communication with such a catheter;

3) second port means for placing the system in fluid communication both with a fluid source means that provides one or more fluids that, during the course of such a procedure, are suctioned into the barrel of the syringe and then injected from the barrel and with a fluid waste disposal means into which waste fluid that has been auctioned into the barrel during the course of such a procedure is injected from the barrel;

4) selectively settable valve means interposed between said first and second port means and said barrel for selectively communicating said first and second port means with said barrel such that in a first selected setting, said valve means communicates said second port means to said barrel while blocking communication of said first port means with said barrel, and in a second selected setting, said valve means blocks communication of said second port means with said barrel while communicating said first port means with said barrel;

5) said plunger has an external actuator for pushing by a person's thumb; and 6) finger grip means that is selectively positionable on the exterior of the barrel to a desired position of comfort for a person's fingers.

* * * * *